United States Patent [19]

Devlin et al.

[11] Patent Number: 4,725,597

[45] Date of Patent: Feb. 16, 1988

[54] BIS(PIPERAZINYL OR HOMOPIPERAZINYL)ALKANES

[75] Inventors: John P. Devlin, Poughkeepsie, N.Y.; Daniel W. McNeil, New Fairfield, Conn.; James J. Keirns; Edward L. Barsumian, both of Danbury, Conn.

[73] Assignee: Boehringer Ingelheim Ltd., Ridgefield, Conn.

[21] Appl. No.: 653,982

[22] Filed: Sep. 24, 1984

Related U.S. Application Data

[63] Continuation-in-part of Ser. No. 477,008, Mar. 21, 1983, abandoned.

[51] Int. Cl.$^4$ .................. A61K 31/495; C07D 403/06
[52] U.S. Cl. .................................. 514/252; 544/357; 540/596
[58] Field of Search .................. 544/357; 514/252

[56] References Cited

U.S. PATENT DOCUMENTS

| | | | |
|---|---|---|---|
| 3,036,076 | 5/1962 | Gabler et al. | 544/337 X |
| 3,901,889 | 8/1975 | Bouchara | 544/357 |
| 4,100,285 | 7/1978 | Murai et al. | 544/357 X |
| 4,166,827 | 9/1979 | Diamond | 544/357 X |

FOREIGN PATENT DOCUMENTS

| | | | |
|---|---|---|---|
| 558875 | 6/1958 | Canada | 544/357 |
| 675224 | 12/1963 | Canada | 544/357 |
| 56-154475 | 11/1981 | Japan | 544/357 |
| 57-140777 | 8/1982 | Japan | 544/357 |

OTHER PUBLICATIONS

Chiavarelli, et al., *Chemical Abstracts*, vol. 63, (1965), entry 8362f.
Dorokhova, et al., *Chemical Abstracts*, vol. 85, (1976), entry 78079g.
Kazakov, et al., *Chemical Abstracts*, vol. 100, (1984), entry 6456h.
Leuscher, et al. I and II, *Chemical Abstracts*, vol. 81, (1974), entries 136184t and 136186v.
Murai, et al., *Chemical Abstracts*, vol. 90, (1979), entry 121652f and 121653g.
Murai, et al., *Chemical Abstracts*, vol. 88, (1978), entry 22979v.

*Primary Examiner*—Donald G. Daus
*Assistant Examiner*—William A. Teoli, Jr.
*Attorney, Agent, or Firm*—David E. Frankhouser; Alan R. Stempel

[57] ABSTRACT

Compounds of the formula

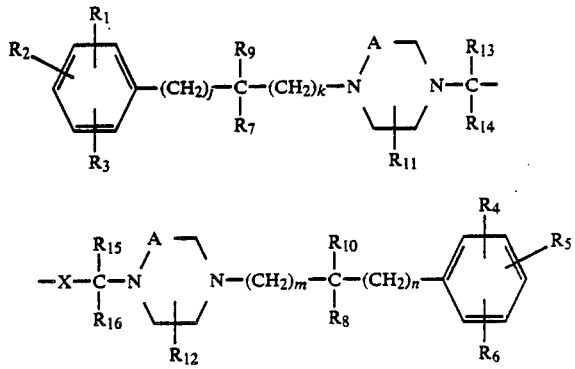

wherein $R_1$, $R_2$, $R_3$, $R_4$, $R_5$, and $R_6$ are independently hydrogen, alkyl of 1 to 4 carbon atoms, hydroxyl, alkoxy of 1 to 4 carbon atoms, alkanoyloxy of 1 to 4 carbon atoms, halogen, trihalomethyl, di(lower alkyl of 1 to 4 carbon atoms)amino, (alkoxy of 1 to 4 carbon atoms)carbonyl, nitro, cyano or alkanoyl of 1 to 3 carbon atoms;

$R_7$ and $R_8$ are independently hydrogen, methyl, hydroxyl, carboxyl, (alkoxy of 1 to 4 carbon atoms)-carbonyl, hydroxymethyl, phenyl, or p-chlorophenyl;

$R_9$ and $R_{10}$ are independently hydrogen or methyl;

j and k are independently 0, 1, 2, or 3, their sum being no more than 4;

m and n are independently 0, 1, 2, or 3, their sum being no more than 4;

A is $-CH_2-$ or $-CH_2-CH_2-$;

$R_7$ and $R_9$ together are oxo, provided k is other than o;

$R_8$ and $R_{10}$ together are oxo, provided m is other than o;

$R_{11}$ and $R_{12}$ independently represent hydrogen or one to four methyl substituents on the carbon atoms of the piperazine ring (A=$-CH_2-$);

$R_{13}$, $R_{14}$, $R_{15}$, and $R_{16}$ are independently hydrogen or methyl;

$R_{13}$ and $R_{14}$ together are oxo; $R_{15}$ and $R_{16}$ together are oxo; and X is alkylene of 1 to 2 carbon atoms, optionally hydroxy-substituted;

or a non-toxic, pharmacologically acceptable acid addition salt thereof, are useful as antiallergic and anti-inflammatory agents.

20 Claims, No Drawings

BIS(PIPERAZINYL OR HOMOPIPERAZINYL)ALKANES

This application is a continuation-in-part of application Ser. No. 6/477,008, filed March 21, 1983 now abandoned.

This invention relates to novel pharmacologically active bis(piperazinyl or homopiperazinyl)alkanes and non-toxic acid addition salts thereof. Also contemplated by this invention are pharmaceutical compositions containing the compounds as active ingredients and methods of using them for the treatment of allergic disorders.

In particular, the present invention relates to novel bis(piperazinyl or homopiperazinyl)alkanes represented by the formula

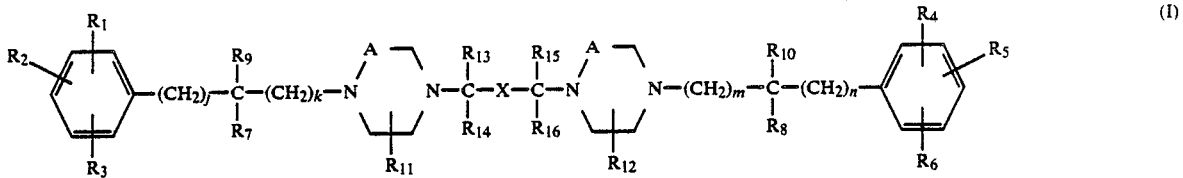

wherein
$R_1$, $R_2$, $R_3$, $R_4$, $R_5$, and $R_6$ are independently hydrogen, alkyl of 1 to 4 carbon atoms, hydroxyl, alkoxy of 1 to 4 carbon atoms, alkanoyloxy of 1 to 4 carbon atoms, halogen, trihalomethyl, di(lower alkyl of 1 to 4 carbon atoms)amino, (alkoxy of 1 to 4 carbon atoms)-carbonyl, nitro, cyano or alkanoyl of 1 to 3 carbon atoms;

$R_7$ and $R_8$ are independently hydrogen, methyl, hydroxyl, carboxyl, (alkoxy of 1 to 4 carbon atoms)carbonyl, hydroxymethyl, phenyl, or p-chlorophenyl;

$R_9$ and $R_{10}$ are independently hydrogen or methyl;
j and k are independently 0, 1, 2, or 3, their sum being no more than 4;
m and n are independently 0, 1, 2, or 3, their sum being no more than 4;
A is —$CH_2$— or —$CH_2$—$CH_2$;

$R_7$ and $R_9$ together are oxo, provided k is other than 0;
$R_8$ and $R_{10}$ together are oxo, provided m is other than 0;
$R_{11}$ and $R_{12}$ independently represent hydrogen or one to four methyl substituents on the carbon atoms of the piperazine ring (A=—$CH_2$—);
$R_{13}$, $R_{14}$, $R_{15}$, and $R_{16}$ are independently hydrogen or methyl;
$R_{13}$ and $R_{14}$ together are oxo;
$R_{15}$ and $R_{16}$ together are oxo; and
X is alkylene of 1 to 2 carbon atoms, optionally hydroxy-substituted;
with the proviso that when $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, and $R_{16}$ are each hydrogen and j, k, m, and n are each 0, X cannot be 1,2-ethylenediol;
or a non-toxic, pharmacologically acceptable acid addition salt thereof.

It will be appreciated by those skilled in the art that, when A in formula I is —$CH_2$—, the compounds of formula I are the piperazines of the formula

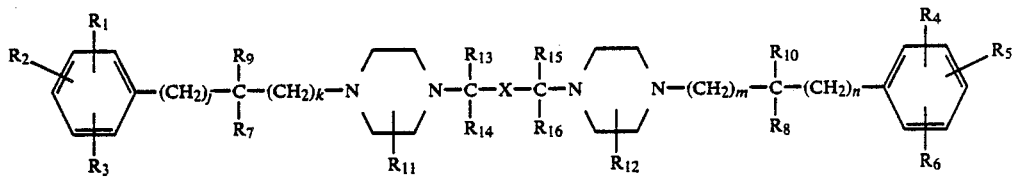

wherein $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, j, k, l, m, and X having the meanings hereinbefore defined with respect to formula I. When A in formula I is —$CH_2CH_2$—, the compounds of formula I are the homopiperazines of the formula

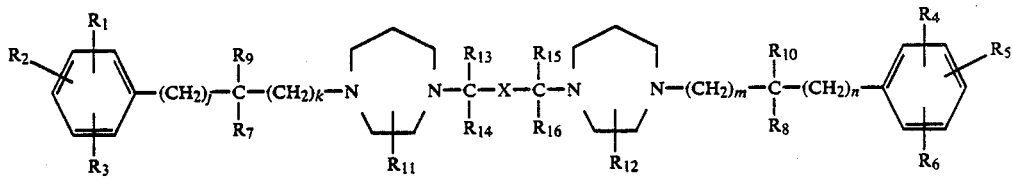

wherein $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}R_{16}$, j, k, m, n, and X have the meanings hereinbefore defined with respect to formula I. The piperazizines of formula Ia are preferred.

In subgeneric aspects, the invention comprehends the following classes of compounds or a non-toxic, pharmaceutically acceptable salt thereof:

A. A compound of the formula

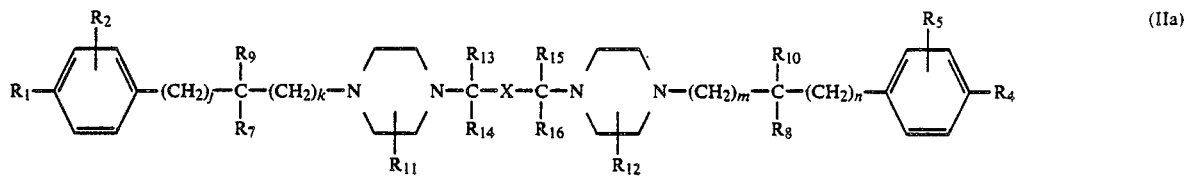
(IIa)

or

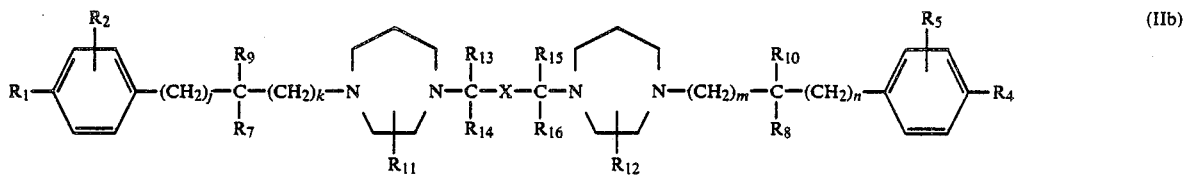
(IIb)

wherein $R_1$, $R_2$, $R_4$, $R_5$, $R_7$, $R_8$, $R_9$, $R_{10}$, $R_{11}$, $R_{12}$, $R_{13}$, $R_{14}$, $R_{15}$, $R_{16}$, j, k, m, n, and X have the meanings hereinbefore defined with respect to formula I.

B. A compound of the formula

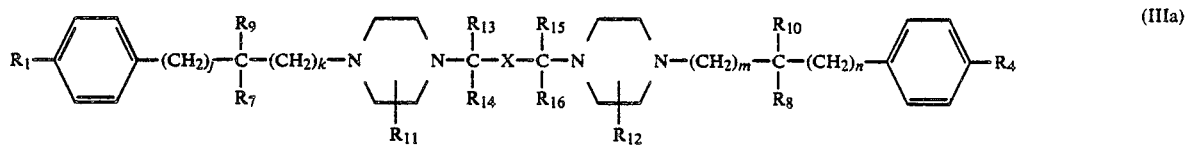
(IIIa)

or

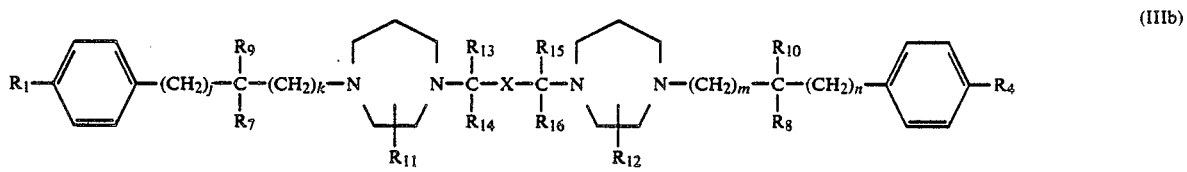
(IIIb)

wherein $R_1$, $R_4$, $R_7$, $R_8$, $R_9$, $R_{10}$, $R_{11}$, $R_{12}$, $R_{13}$, $R_{14}$, $R_{15}$, $R_{16}$, j, k, m, n, and X have the meanings hereinbefore defined with respect to formula I.

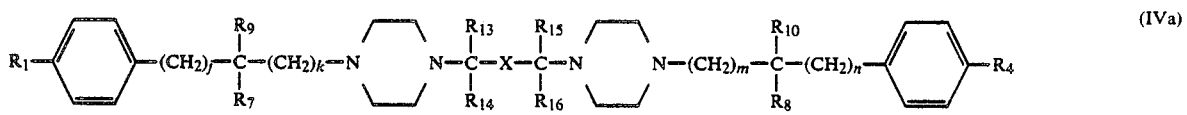
(IVa)

or

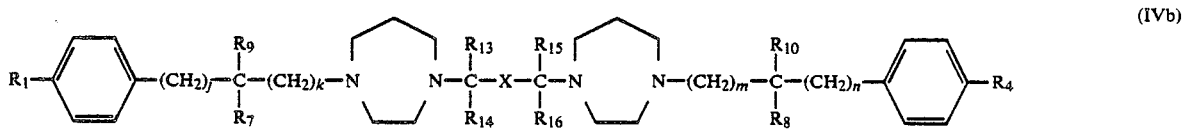
(IVb)

wherein $R_1$, $R_4$, $R_7$, $R_8$, $R_9$, $R_{10}$, $R_{13}$, $R_{14}$, $R_{15}$, $R_{16}$, j, k, m, n, and X have the meanings hereinbefore defined with respect to formula I.

The preferred compounds of formulas I, Ia, Ib, IIa, IIb, IIIa, IIIb, IVa, or IVb are those wherein $R_1$ or $R_4$ is a group other than hydrogen, preferably a group selected from chlorine, alkyl of 1 to 4 carbon atoms, or alkoxy of 1 to 4 carbon atoms. Chlorine is most preferred. A preferred subgenus comprehends the compounds of the formula

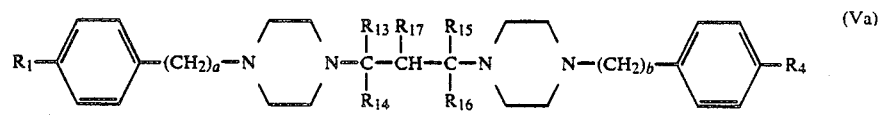
(Va)

or

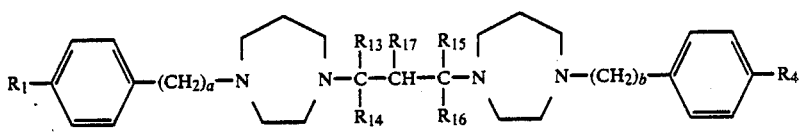

wherein $R_1$ and $R_4$ independently are chlorine, alkyl of from 1 to 4 carbon atoms, or alkoxy of from 1 to 4 carbon atoms; $R_{13}$ and $R_{14}$ are hydrogen, or together, are oxo; $R_{15}$ and $R_{16}$ are hydrogen, or together, are oxo; $R_{17}$ is hydrogen or hydroxyl; and a and b are independently 1, 2, 3, or 4.

Particularly preferred are the compounds of formulas Va are or Vb wherein (1) $R_1$ and $R_4$ are each $R_1$ and $R_4$ are chlorine; $R_{13}$ and $R_{14}$ are hydrogen, or together, are oxo; $R_{15}$ and $R_{16}$ are hydrogen, or together, are oxo; $R_{17}$ is hydrogen or hydroxy; and a and b are independently 1, 2, 3, or 4, and (2) $R_1$ and $R_4$ are each chlorine; $R_{13}$, $R_{14}$, $R_{15}$, $R_{16}$, and $R_{17}$ are each hydrogen; and a and b are independently 1, 2, 3, or 4.

The compounds of formula I are capable of inhibiting in vitro the IgE-mediated release of histamine from human peripheral blood leukocytes (basophils), from guinea pig basophils, and from rat peritoneal mast cells, and are useful in warm-blooded animals for inhibiting the antigen-induced cellular release of histamine and/or other mediators of the allergic reaction. The compounds of formula I can be used for the treatment of allergic disorders, such as allergic asthma, allergic rhinitis, allergic conjunctivitis, hay fever, urticaria, food allergies, and the like.

By virtue of their ability to inhibit cellular mediator release, the compounds may also be useful for the treatment of inflammatory or immunological disorders.

For pharmaceutical purposes as antiallergic agents, the compounds of the present invention are administered topically to the skin or preferably to the mucosa of the eye, nose, or respiratory tract in conventional pharmaceutical compositions, that is, compositions comprising an inert pharmaceutical carrier and an effective amount of the active ingredient.

For administration to the respiratory tract, the compounds can be administered as an aerosol or solution for a nebulizer, or as a microfine powder for insufflation, alone or in combination with an inert carrier such as lactose. In such a case the particles of active compounds suitably have diameters of less than 20 microns, preferably less than 10 microns. Where appropriate, small amounts of other antiallergic and antiasthmatic bronchodilators, for examples sympathomimetic amines such as isoprenaline, isoetharine, metaproterenol, salbutamol, phenylephrine, fenoterol and phedrine; xanthine derivatives such as theophylline and aminophylline; and corticosteroids such as prednisolone and adrenal stimulants such as ACTH may be included.

For administration to the skin, the compounds can be administered as an ointment, cream, lotion, gel, or aerosol. Solutions for topical application to the nose can conveniently be administered by nasal sprays or drops. In addition, a sterile solution or ointment can be formulated for application to the eye.

Topical solutions for the nose and the eye may contain, in addition to the compounds of this invention, suitable buffers, tonicity adjusters, microbial preservatives, antioxidants and viscosity-increasing agents in an aqueous vehicle. Examples of agents used to increase viscosity are polyvinyl alcohol, cellulose derivatives, polyvinylpyrrolidone, polysorbates or glycerin. Microbial preservatives added may include benzylkonium chloride, thimerosal, chlorobutanol or phenylethyl alcohol. Topical preparations for the eye may also be prepared as ointments in a suitable inert base consisting of mineral oil, petrolatum, polyethylene glycols or lanolin derivatives, along with microbial preservatives.

Solutions for the topical administration of the compounds of formula I to the eye or nasal mucosa can preferably contain about 0.005% to about 1% (w/w) of the active ingredient, depending upon the solubility of the particular compound and the desired pH of the solution. For example, with the preferred compound 1,3-bis[4-(3-(4-chlorophenyl)propyl)-1-piperazinyl]propane, as the tetrahydrochloride monohydrate salt (Example 24) the solubility limit is 0.1% at pH 7.

Ointments for topical administration to the skin can preferably contain about 0.1% to about 5% (w/w) of the active ingredient.

The topical formulations containing the active ingredients can be administered as needed depending upon the nature and severity of the allergic disorder being treated. In general, the formulations can be applied topically one to four times per day.

The topical formulations employing the compounds of formula I as active ingredients can be prepared using conventional pharmaceutical techniques which will be readily apparent to those skilled in the pharmaceutical arts.

The compounds of formula I can be prepared according to the following methods:

Method A

Reaction of one equivalent of a compound of the formula

wherein $R_{13}$, $R_{14}$, $R_{15}$, $R_{16}$ and X have the meanings defined above, and Y and Z are reactive groups which will react with an amine to form a carbon-nitrogen bond, for example, chloro, bromo, iodo, activated ester, hydroxyl, sulfuric ester, sulfonic ester or the like, with at least two equivalents of a compound of the formula

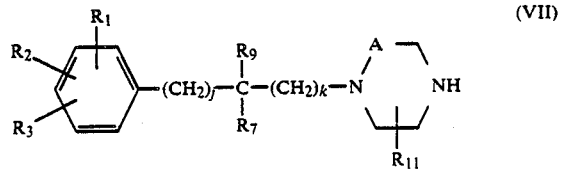

wherein $R_1$, $R_2$, $R_3$, $R_7$, $R_9$, $R_{11}$, j, k and A have the meanings defined above.

Only symmetrical compounds of the formula I are obtainable by this method.

Method B

Reaction of a compound of the formula

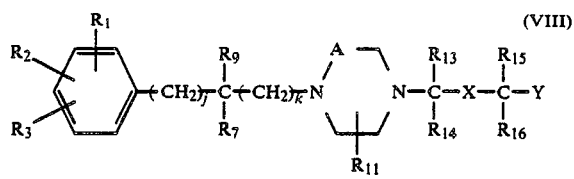

wherein $R_1$, $R_2$, $R_3$, $R_7$, $R_9$, $R_{11}$, $R_{13}$, $R_{14}$, $R_{15}$, $R_{16}$, X, Y, j, k and A have the meanings defined above, with a compound of the formula

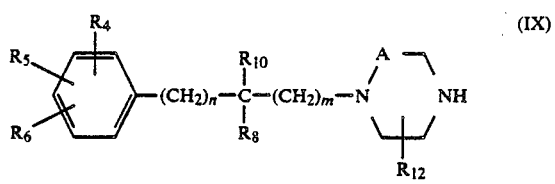

wherein $R_4$, $R_5$, $R_6$, $R_8$, $R_{10}$, $R_{12}$, m, n and A have the meanings defined above. Both symetrical and unsymmetrical compounds may be prepared by this method.

Method C

Compounds which are symmetric around the central X grouping of formula may be prepared by reaction of a compound of the formula

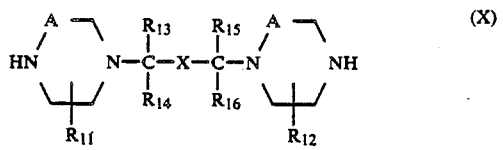

wherein $R_{11}$, $R_{12}$, $R_{13}$, $R_{14}$, $R_{15}$, $R_{16}$, X and A have the meanings defined above, with a compound of the formula

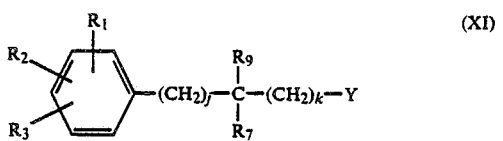

wherein $R_1$, $R_2$, $R_3$, $R_7$, $R_9$, Y, j and k have the meanings defined above.

Method D

Compounds wherein the variable X in formula I is a carbinol moiety may also be prepared by reaction of a compound of the formula

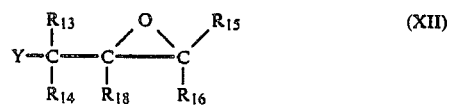

wherein $R_{13}$, $R_{14}$, $R_{15}$ and $R_{16}$ have the meanings previously defined, $R_{18}$ is hydrogen or lower alkyl, and Y has the same meanings as in formula VI, with a compound of the formula IX.

The condensation reactions described in method A to D may be performed in the presence or absence of a solvent. Aqueous or organic inert solvents, depending on the nature of the reactants, may be employed. Such solvents include dimethylsulfoxide, dimethylformamide, dioxane, ethoxyethanol and alkanols containing up to five carbon atoms, with or without the addition of water. Aromatic hydrocarbons may also be employed. It is preferred but not essential, to perform the reaction in the presence of an acid-binding agent such as triethylamine, an alkali metal carbonate or an alkali metal hydroxide.

The reaction temperature depends on the starting compounds and on the solvent which is used for the reaction and lies between room temperature and the reflux temperature of the reaction mixture. The reaction time is temperature-dependent and may be several minutes to many hours.

In cases wherein an end product of the formula I $R_7$ and/or $R_8$ are hydroxyl, a compound wherein $R_7$ and $R_9$ and/or $R_8$ and $R_{10}$ together are oxo may be hydrogenated with conventional hydrogenating agents, such as sodium borohydride, in a manner known per se to obtain the corresponding hydroxy-substituted compound. The free hydroxyl group may subsequently be alkylated or acylated by conventional methods.

The compounds embraced by formula I are basic and therefore form addition salts with inorganic or organic acids. Examples of non-toxic, pharmacologically acceptable acid addition salts are those formed with a hydrohalic acid, especially hydrochloric or hydrobromic acid, nitric acid, sulfuric acid, o-phosphoric acid, citric acid, maleic acid, fumaric acid, propionic acid, butyric acid, acetic acid, succinic acid, methanesulfonic acid, benzenesulfonic acid, p-toluenesulfonic acid, or the like.

The starting compounds for methods A to D are known compounds or may be prepared by known methods.

Thus, compounds of the formula VII are described in British Pat. No. 480,358 and J. Am. Chem. Soc., 66, 263 (1944).

The synthesis of compounds of the formula VIII is known from numerous publications, such as Helv.-Chim.Acta 41, 1072 (1958) or Monatshefte 87, 701 (1956).

Compounds of the formula X are disclosed in British Pat. No. 480,358 and Khim.-Farm.Zh. 10, 36 (1976), abstracted in C.A. 85, 78079.

The following examples illustrate the present invention and will enable others skilled in the art to understand it more completely. It should be understood, however, that the invention is not limited solely to the particular examples given below.

EXAMPLE 1

1,3-Bis[4-(4-chlorobenzyl)-1-piperazinyl]propane tetrahydrochloride

A mixture of 10.5 g of 1-(4-chlorobenzyl) piperazine, 9.5 g of 1-bromo-3-chloropropane, and 100 ml of reagent ethanol was refluxed for 17 hours. The solvent was then removed by rotary evaporation. The resulting oil was mixed with 200 ml of 1M dibasic potassium phosphate. Solid tribasic sodium phosphate was slowly added until the pH rose above 9. This mixture was extracted 5 times with 50 ml portions of ether. The ether was evaporated, and the residue was acidified with 100 ml of 2M phosphoric acid and filtered. The aqueous filtrate was then made basic with 2N sodium hydroxide, again extracted into ether (250 ml) and dried over magnesium sulfate. The product was precipitated with gaseous hydrogen chloride and recrystallized from reagent ethanol/water to give 5.8 g (39% of theory) of 1,3-bis[4-(4-chlorobenzyl)-1-piperazinyl]propane tetrahydrochloride as a white crystalline solid (m.p. 261°–274° C., with decomp.).

EXAMPLE 2

1,3-Bis[4-(4-chlorobenzyl)-1-piperazinyl]-2-hydroxypropane

A mixture of 4.4 g of epichlorohydrin, 20.1 g of 1-(4-chlorobenzyl)piperazine, 6.0 g of triethylamine and 50 g of reagent ethanol was refluxed for 3 days. The solvent was removed from the reaction mixture by rotary evaporation, and the residue was then made basic with 2N sodium hydroxide and extracted with ether (5 × 100 ml). The ether extract was dried over magnesium sulfate and evaporated, leaving an oil which solidified on standing. Recrystallization from heptane resulted in the isolation of 18.6 g (82% of theory) of 1,3-bis[4-(4-chlorobenzyl)-1-piperazinyl]-2-hydroxypropane as a colorless crystalline solid (m.p. 85°–86.5° C.)

EXAMPLE 3

1,4-Bis[4-(4-chlorobenzyl)-1-piperazinyl]butane hemihydrate

A mixture of 2.2 g of 1,4-dibromobutane, 4.2 g of 1-(4-chlorobenzyl)piperazine, 2.8 g of anhydrous potassium carbonate and 20 ml of reagent ethanol was refluxed for 18 hours. The solvent was evaporated under reduced pressure, and the residual oil was heated for 16 hours at 160° C. The product was dissolved in 50 ml of hot water and extracted with ether (3 × 80 ml). The ether extract was concentrated to an oil which was chromatographed on a silica column, the eluant being $CH_2Cl_2/CH_3OH$/ammonium hydroxide (45:5:1). The resulting brown solid was dissolved in acetone and precipitated with water to give 0.8 g (35% of theory) of 1,4-bis[4-(4-chlorobenzyl)-1-piperazinyl]butane hemihydrate as a white crystalline solid (m.p. 101°–103° C.).

EXAMPLE 4

1,3-Bis(4-benzyl-1-piperazinyl)propane tetrahydrochloride

A mixture of 7.0 g of 1-benzylpiperazine, 3.2 g of 1-bromo-3-chloropropane, 4.0 g of triethylamine and 100 ml of reagent ethanol was refluxed for 2½ hours. The reaction mixture was then poured into 1 liter of ether, and the precipitated triethylamine salt was filtered off. The filtrate was evaporated to leave a yellow oil, which was dissolved in 100 ml of heptane and filtered. The solvent was removed by rotary evaporation, and the residue was redissolved in 150 ml of ether. Addition of excess anhydrous hydrogen chloride precipitated 8.8 g (82% of theory) of 1,3-bis(4-benzyl-1-piperazinyl)propane tetrahydrochloride as a white crystalline solid (m.p. 250°–265° C.).

EXAMPLE 5

1,3-Bis[4-(4-fluorobenzyl)-1-piperazinyl]propane tetrahydrochloride (a) A solution of 29 g of p-fluorobenzyl chloride in 50 g of reagent ethanol was added dropwise to a stirred solution of 34.5 g of piperazine in 150 g of reagent ethanol. A cold water bath was used to maintain the reaction temperature at 20° C. during the addition. The reaction mixture was stirred for an additional 1½ hours and then added to 2 liters of ether. Precipitated piperazine hydrochloride was filtered off. The filtrate was concentrated to an oil, which was chromatographed on a silica column, the eluant being a mixture of $CH_2Cl_2$/methanol/ammonium hydroxide in the ratio of 45:5:1. After concentration of appropriate fractions, 21.7 g of 1-(4-fluorobenzyl)piperazine were isolated as a colorless liquid (56% of theory).

(b) A mixture of 5.8 g of 1-(4-fluorobenzyl)piperazine, 3.2 g of 1-bromo-3-chloropropane, 4.0 g of triethylamine and 50 ml of reagent ethanol was refluxed for 3 hours and then poured into 1 liter of ether. The precipitate was filtered off, and the filtrate was evaporated to an oil. This oil was dissolved in 100 ml of ether and precipitated with excess anhydrous hydrogen chloride. Recrystallization from ethanol/water gave 3.3 g (29% of theory) of 1,3-bis[4-(4-fluorobenzyl)-1-piperazinyl]propane tetrahydrochloride as a white crystalline solid (m.p. 228°–237° C., with decomp.).

EXAMPLE 6

1,3-Bis[4-(4-chloro-benzyl)-1-piperazinyl]-1-oxo-propane trihydrochloride

A mixture of 2.0 g of 1-(4-chlorobenzyl)piperazine, 1.0 g of triethylamine, 20 g of xylene and 0.8 g of 3-bromopropionyl chloride was refluxed for 18 hours. The reaction mixture was filtered, and the filtrate was mixed with excess hydrogen chloride-saturated ether until the mixture tested acidic to litmus. The resulting precipitate was filtered off and recrystallized from ethanol/water to yield 1.2 g (45% of theory) of 1,3-bis[4-(4-chlorobenzyl)-1-piperazinyl]-1-oxopropane trihydrochloride as a white crystalline solid (m.p. 222°–250° C., with decomp.).

EXAMPLE 7

1,3-Bis[4-(4-chlorobenzyl)-1-piperazinyl]-1-methylpropane tetrahydrochloride hemihydrate A mixture of 7.3 g of 1-(4-chlorobenzyl)piperazine, 2.8 g of 1,3-dibromobutane, 11.0 g of triethylamine and 50 ml of reagent ethanol was refluxed for 48 hours. The solvent was removed by rotary evaporation. The residue was mixed with 100 ml of toluene and then refluxed for 24 hours. The mixture was then poured into 1 liter of ether and filtered. The filtrate was evaporated to an oil, which was chromatographed on silica with $CH_2Cl_2/CH_3OH$/ammonium hydroxide (45:5:1) as the eluant. The resulting oil was dissolved in 100 ml of ether and precipitated with excess anhydrous hydrogen chloride. This product was dissolved in water and precipitated by addition of acetone to give 1.2 g (11% of theory) of 1,3-bis[4-(4-chlorobenzyl)-1-piperazinyl]-1-methylpropane tetrahydrochloride hemihydrate as a white crystalline product (m.p. 228°–232° C.).

EXAMPLE 8

1,3-Bis[4-(4-chlorobenzhydryl)-1-piperazinyl]-propane dihydrochloride dihydrate

A mixture of 7.4 g of N-(p-chlorobenzhydryl)-piperazine, 2.0 g of 1-bromo-3-chloropropane, 1.6 g of triethylamine and 25 g of reageant ethanol were refluxed for 18 hours. The reaction mixture was made basic with 5N sodium hydroxide and extracted with methylene chloride (5×50 ml). The extract was dried over magnesium sulfate, and hydrogen chloride-saturated ether was added until the mixture tested acid to litmus. The precipitated crude 1,3-bis[4-(4-chlorobenzhydryl) 1-piperazinyl]propane dihydrochloride dihydrate (2.5 g, 27% of theory) was filtered off. Purification by dissolution in methylene chloride followed by precipitation by addition of ether resulted in a white crystalline product (m.p. 163°-196° C., with decomp.).

EXAMPLE 9

1-[4-(4-Chlorobenzyl)1-piperazinyl]-3-[4-(2-ethoxycarbonyl-2-phenylethyl]-propane tetrahydrochloride monohydrate (a) A mixture of 1.8 g of ethyl atropate and 0.9 g of piperazine was stirred in a round-bottom flask. When the exothermic reaction abated, the mixture was heated to 80° C. and stirred for an additional 20 minutes. The reaction mixture was then allowed to stand overnight at room temperature. The resulting solid was chromatographed on a silica column using ether as the eluant, followed by $CH_2Cl_2/CH_3OH$/ammonium hydroxide (45:5:1). The 1-(2-ethoxycarbonyl-2-phenylethyl)-piperazine product (0.75 g, 29% of theory) came off the column with the second eluant and was used in the following step without further purification.

(b) A mixture of 3.0 g of 1-chloro-3-[4-(4-chlorobenzyl)-1-piperazinyl)propane, 3.5 g of triethylamine, 3.7 g of 1-(2-ethoxycarbonyl-2-phenylethyl)piperazine and 50 ml of reagent ethanol was refluxed for 2 hours and was then poured into 1 liter of ether. The resulting mixture was filtered, and the filtrate was evaporated to an oil. This oil was purified by chromatography on a silica column, the eluant being $CH_2Cl_2/CH_3OH$/ammonium hydroxide (45:5:1), to yield 3.0 g of an oil. This oil was dissolved in 150 ml of ether and precipitated with excess anhydrous hydrogen chloride to give 3.4 g of a solid. This product was re-chromatographed on silica using ether as the first eluant, then switching to the above methylene chloride mixture. The resulting product was converted into its hydrochloride as above, dissolved in water and precipitated by addition of acetone, to yield 1.1 g (15% of theory) of 1-[4-(4-chlorobenzyl)-1-piperazinyl]-3-[4-(2-ethoxycarbonyl-2-phenylethyl)-1-piperazinyl]propane tetrahydrochloride monohydrate as a white crystalline product (m.p. 198°-2°-°° C.).

EXAMPLE 10

1-[4-(4-Chlorobenzyl)-1-piperazinyl]-3-(4-phenacyl-1-piperazinyl)propane tetrahydrochloride monohydrate A mixture of 4.1 g of 1-phenacylpiperazine, 5.7 g of 1-chloro-3-[4-(4-chlorobenzyl)-1-piperazinyl]propane, 2.6 g of triethylamine and 35 ml of reagent ethanol was refluxed for 5 hours. The solvent was removed by rotary evaporation, 150 ml of water were added, and the mixture was extracted with ether (3×150 ml). The ether solution was evaporated to an oil, which was chromatographed on a silica column, the eluant being $CH_2Cl_2/CH_3OH$/ammonium hydroxide (45:5:1), to yield crude 1-[4-(4-chlorobenzyl)-1-piperazinyl]-3-(4-phenacyl-1-piperazinyl)propane (7.0 g, 50% of theory). This oil was dissolved in 200 ml of ether and precipitated with excess anhydrous hydrogen chloride. The precipitate was then dissolved in water and re-precipitated by addition of acetone to give 1-[4-(4-chlorobenzyl)-1-piperazinyl]-3-(4-phenacyl-1-piperazinyl)propane tetrahydrochloride monohydrate as a white crystalline product (m.p. 211°-218° C.).

EXAMPLE 11

1-[4-(4-Chlorobenzyl)-1-piperazinyl]-3-[4-(2-hydroxy-2-phenylethyl)-1-piperazinyl]propane tetrahydrochloride A solution of 3.0 g of 1-[4-chlorobenzyl)-1-piperazinyl]-3-(4-phenacyl-1-piperazinyl)propane in 50 ml of reagent ethanol was mixed with 3.0 g of sodium borohydride. The mixture was stirred for 4 hours, and then the unreacted sodium borohydride was destroyed by the addition of 25 ml of acetone. The solvents were removed under vacuum, and 50 ml of water were added. The mixture was extracted with ether (3×250 ml). The extract was evaporated to an oil, which was chromatographed on a silica column, the eluant being $CH_2Cl_2/CH_3OH$/ammonium hydroxide (45:5:1). The fractions containing the desired product were combined and evaporated to an oil, which was dissolved in 100 ml of ether and precipitated by addition of excess anhydrous hydrogen chloride. The resulting solid was dissolved in water and precipitated with acetone to give 0.65 g (16% of theory) of 1-[4-(4-chlorobenzyl-1-piperazinyl]-3-[4-(2-hydroxy-2-phenylethyl)-1-piperazinyl]propane tetrahydrochloride as a white crystalline product (m.p. 240°-248° C., with decomp.).

EXAMPLE 12

1,3-Bis(4-phenacyl-1-piperazinyl)propane tetrahydrochloride monohydrate

A mixture of 6.1 g of 1-phenacylpiperazine, 2.4 g of 1-bromo-3-chloropropane, 3.1 g of triethylamine and 50 ml of reagent ethanol was refluxed for 3 hours and then evaporated to an oil. Water (250 ml) was added, and the mixture was extracted with ether (3×150 ml). After evaporation of the ether, the residual oil was chromatographed on silica, the eluant being $CH_2Cl_2/CH_3OH$/ammonium hydroxide (45:5:1). The high purity fractions were combined and evaporated to an oil, which was dissolved in 150 ml of ether and precipitated with excess anhydrous hydrogen chloride. This solid was dissolved in water and precipitated by addition of acetone to give 1.3 g (14% of theory) of 1,3-bis-(4-phenacyl-1-piperazinyl)propane tetrahydrochloride monohydrate as a white crystalline product (m.p. 194°-204° C.).

EXAMPLE 13

1,3-Bis[4-(2-phenyl-2-hydroxyethyl)-1-piperazinyl]propane tetrahydrochloride

A solution of 2.5 g of 1,3-bis(4-phenacyl-1-piperazinyl)propane in 50 ml of reagent ethanol was mixed with 2.5 g of sodium borohydride and stirred for 4 hours. Residual sodium borohydride was destroyed by the addition of 25 ml of acetone, and then the solvents were removed by rotary evaporation. Water (50 ml) was added, and the mixture was extracted with ether (3×150 ml). After evaporation of the ether, the product was chromatographed on silica, the eluant being CH$_2$Cl$_2$/CH$_3$OH/ammonium hydroxide (45:5:1). The resulting oil was dissolved in 100 ml of ether and precipitated by addition of excess anhydrous hydrogen chloride to yield 0.75 g (22% of theory) of 1,3-bis[4-(2-phenyl-2-hydroxyethyl)-1-piperazinyl]propane tetrahydrochloride as a white crystalline product (m.p. 233°–240° C.).

EXAMPLE 14

1,3-Bis(4-phenethyl-1-piperazinyl)propane dihydrochloride dihydrate

A mixture of 5.7 g of 1-phenethylpiperazine, 2.4 g of 1-bromo-3-chloropropane, 4.1 g of triethylamine and 30 ml of reagent ethanol was refluxed for 3 hours. 50 ml of water were then added, and the mixture was concentrated to about 40 ml by rotary evaporation. The resulting mixture was extracted with ether (3×150 ml), and the extract was evaporated to a brown oil. This oil was dissolved in 150 ml of ether and was precipitated by addition of excess anhydrous hydrogen chloride. The precipitate was dissolved in water and reprecipitated by the addition of acetone to give 3.1 g (37% of theory) of 1,3-bis(4-phenethyl-1-piperazinyl)propane dihydrochloride dihydrate as a white crystalline product (m.p. 210°–225° C.).

EXAMPLE 15

1,3-Bis[4-(4-chlorobenzyl)-1-piperazinyl]-1,3-dioxopropane dihydrochloride monohydrate A mixture of 4.2 g of 1-(4-chlorobenzyl)piperazine, 1.4 g of malonyl dichloride, 10 g of methylene chloride and 2.0 g of triethylamine was stirred for 60 hours. The reaction mixture was made basic with 2N sodium hydroxide. The organic layer was separated, and the aqueous phase was extracted with three 50 ml portions of ether, followed by three 50 ml portions of methylene chloride. The organic phases were combined and mixed with 100 ml of 2N hydrochloric acid. The aqueous phase was separated and made basic with 2N sodium hydroxide solution. The resulting oil was collected and chromatographed on silica, the eluant being CH$_2$Cl$_2$/CH$_2$OH/ammonium hydroxide (200:5:1). The appropriate fractions were combined, evaporated to an oil, dissolved in 100 ml of ether and precipitated with excess anhydrous hydrogen chloride. The precipitate was recrystallized from reagent ethanol to yield 1.3 g (22% of theory) of 1,3-bis[4-(4 -chlorobenzyl)-1-piperazinyl]-1,3-dioxopropane dihydrochloride monohydrate as a very slightly yellow crystalline solid (m.p. 199°–206° C.).

EXAMPLE 16

1,3-Bis[4-(4-chlorophenethyl)-1-piperazinyl]propane

A mixture of 6.7 g of 1-(4- chlorophenethyl) piperazine, 2.4 g of 1-bromo-3-chloropropane, 3.1 g of triethylamine and 20 ml of reagent ethanol was refluxed for 3 hours. The reaction mixture was diluted with 50 ml of water and then concentrated to about 50 ml by rotary evaporation. The resulting mixture was extracted with ether (3×150 ml), and the extract was evaporated to give a colorless solid which was recrystallized from heptane to yield 3.3 g (45% of theory) of 1,3-bis[4-(4-chlorophenethyl)-1-piperazinyl]propane as a white crystalline product (m.p. 87°–88° C.).

EXAMPLE 17

1,3-Bis[4-(1-phenylethyl)-1-piperazinyl]-propane tetrahydrochloride

A mixture of 7.6 g of 1-(1-phenylethyl)piperazine, 3.2 g of 1-bromo-3-chloropropane and 50 ml of reagent ethanol was refluxed for 5 hours. The solvent was then removed under vacuum, 75 ml of water were added, and the mixture was extracted with ether (3×150 ml). The ether extract was evaporated to an oil and chromatographed on silica, the eluant being CH$_2$Cl$_2$/CH$_3$OH/ammonium hydroxide (45:5:1). The resulting yellow oil was dissolved in 150 ml of ether and precipitated with excess anhydrous hydrogen chloride to yield 6.1 g (51% of theory) of 1,3-bis[4-(1-phenylethyl) -1-piperazinyl]propane tetrahydrochloride. The product was recrystallized from ethanol/water to yield a white crystalline solid (m.p. 236°–246° C., with decomp.).

EXAMPLE 18

1,3-Bis[4-(4-chlorobenzyl)-2,5-dimethyl-1-piperazinyl] propane tetrahydrochloride dihydrate (a) A solution of 16 g of p-chlorobenzyl chloride in 75 ml of reagent ethanol was added dropwise to a solution of 25 g of 2,5-dimethylpiperazine in 75 ml of reagent ethanol. The mixture was stirred overnight and then filtered. The solvent was removed from the filtrate by vacuum. The residue was extracted with ether (3×350 ml), and the extract was evaporated to an oil and chromatographed on silica, the eluant being CH$_2$Cl$_2$/CH$_3$OH/ammonium hydroxide (45:5:1). This yielded 9.1 g (38% of theory) of 1-(4-chlorobenzyl)-2,5-dimethylpiperazine as a colorless liquid which was used in the following step.

(b) A mixture of 6.0 g of 1-(4-chlorobenzyl)-2,5-dimethyl-piperazine, 2.0 g of 1-bromo-3-chloropropane, 3.2 g of triethylamine and 50 ml of reagent ethanol was refluxed for 6 hours. The solvent was then removed under vacuum, 50 ml of water were added, and the mixture was extracted with ether (3×150 ml). The extract was then evaporated to an oil and chromatographed on silica, the eluant being CH$_2$Cl$_2$/CH$_3$OH/ammonium hydroxide (45:5:1). The product was dissolved in 150 ml of ether and precipitated with excess anhydrous hydrogen chloride. The precipitate was dissolved in water and reprecipitated by addition of acetone to give 0.7 g of 1,3-bis[4-(4-chlorobenzyl)-2,5-dimethyl-1-piperazinyl]propane tetrahydrochloride dihydrate as a white crystalline product (m.p. 204°–214° C.).

EXAMPLE 19

1,3-Bis[4-(4-methoxybenzyl)-1-piperazinyl]propane

A mixture of 4.1 g of 1-(p-methoxybenzyl)piperazine, 1.6 g of 1-bromo-3-chloropropane, 25 ml of reagent ethanol and 2.5 ml of triethylamine was refluxed for 5 hours. The resulting mixture was evaporated under vacuum, and the residue was mixed with 25 ml of water and extracted with ether. The extract was evaporated to a yellow oil which solidified on standing. Recrystallization twice from heptane resulted in 2.3 g (51% of theory) of 1,3-bis[4-(4-methoxy-benzyl)-1-piperazinyl]propane as a white crystalline solid (m.p. 86°–87° C.).

EXAMPLE 20

1,3-Bis[4-(3,4-dichlorobenzyl)-1-piperazinyl]-propane tetrahydrochloride

A mixture of 5.2 g of 1-(3,4-dichlorobenzyl) piperazine, 2.2 g of 1-bromo-3-chloropropane, 3.0 g of triethylamine and 20 g of reagent ethanol was refluxed. After 1 hour an additional 0.06 g of 1-bromo-3-chloro-propane was added, and after another hour another 0.06 g of the dihalide was added. The mixture was refluxed overnight and then evaporated under vacuum to yield a gummy solid which was mixed with 150 ml of ether and filtered. The filtrate was dried over magnesium sulfate. Hydrogen chloride-saturated ether was added to the filtrate until the mixture remained acidic when tested with litmus. The resulting precipitate was dissolved in a minimum amount of water. Concentrated hydrochloric acid was then added dropwise, forming a heavy precipitate. Addition was continued until no further precipitation occurred. Filtration and drying under vacuum resulted in 4,5 g (44% of theory) of 1,3-bis[4-(3,4-dichlorobenzyl)-1-piperazinyl]propane tetrahydrochloride as white needles (m.p. 245°-251° C., with decomp.).

EXAMPLE 21

1,3-Bis[4-(2-chlorobenzyl)-1-piperazinyl]propane tetrahydrochloride

A mixture of 8.4 g of 1 (2-chlorobenzyl)piperazine, 3.2 g of 1-bromo-3-chloropropane, 4.0 g of triethylamine and 30 g of reagent ethanol was refluxed overnight. The solvent was evaporated under vacuum, and the residue was mixed with 150 ml of ether and filtered. The filtrate was dried over magnesium sulfate. Hydrogen chloride-saturated ether was then slowly added to the dry filtrate until the resulting mixture tested acidic to litmus. The resulting precipitate was filtered off, dried and weighed. This yielded 6.1 g (50% of theory) of crude 1,3-bis[4-(2-chlorobenzyl)-1-piperazinyl]propane tetrachloride. Recrystallization from ethanol/water yielded a white crystalline solid (m.p. 251°-255° C.).

EXAMPLE 22

1,3-Bis[4-(4-methylbenzyl)-1-piperazinyl]-propane tetrahydrochloride

A mixture of 5.7 g of 1-(4-methylbenzyl)piperazine, 2.4 g of 1-bromo-3-chloropropane, 25 ml of reagent ethanol and 3.0 g of triethylamine was refluxed for 5 hours. The solvent was removed under vacuum, and the residue was mixed with 40 ml of water. The resulting aqueous mixture was extracted with ether (3×150 ml). Evaporation of the ether resulted in a light yellow oil which solidified on standing. This product was dissolved in 50 ml of ether, and hydrogen chloride-saturated ether was added until the mixture tested acidic to litmus. The resulting precipitate was dissolved in 20 ml of water, and acetone was added until product ceased coming out of solution. This yielded 5.8 g (68% of theory) of 1,3-bis[4-(4-methylbenzyl)-1-piperazinyl]-propane tetrahydrochloride as a white crystalline product (m.p. 245°-252° C., with decomp.).

EXAMPLE 23

1,3-Bis[4-(3-chlorobenzyl)-1-piperazinyl]propane dihydrochloride monohydrate

A mixture of 6.3 g of 1-(3-chlorobenzyl)piperazine, 2.4 g of 1-bromo-3-chloropropane, 50 ml of reagent ethanol and 3.0 g of triethylamine was refluxed for 4 hours. Water (70 ml) was added, and the mixture was concentrated under vacuum to about 70 ml. The resulting aqueous mixture was extracted with ether (3×150 ml), and the extract was concentrated under vacuum to give a reddish-yellow oil. Chromatography of this oil on a silica column, the eluant being $CH_2Cl_2/CH_3OH$/ammonium hydroxide (45:5:1), resulted in an oil which was dissolved in 50 ml of ethanol. Hydrogen chloride-saturated ether was added to this solution until the mixture tested acidic to litmus. The resulting precipitate was filtered off, dried and weighed to yield 5.6 g (68% of theory) of 1,3-bis[4-(3-chlorobenzyl)-1-piperazinyl]-propane dihydrochloride monohydrate. Recrystallization from water gave a white crystalline solid (m.p. 248°-257° C., with decomp.).

EXAMPLE 24

1,3-Bis[4-(3-{4-chlorophenyl}propyl)-1-piperazinyl]-propane tetrahydrochloride monohydrate (a) A mixture of 40.6 g of 3-(4-chlorophenyl)propyl chloride, 130.0 g of anhydrous piperazine and 550 ml of reagent ethanol was refluxed for 2 hours. Solvent was removed under vacuum and the residue was chromatographed on silica with the eluant being $CH_2Cl_2/CH_3OH$/ammonium hydroxide (45:5:1). Appropriate fractions were combined, concentrated to an oil, mixed with 1400 ml 1N HCl and filtered. The filtrate was brought to pH 10 with concentrated aqueous NaOH and then extracted with ether (4×200 ml). The extract was dried over $MgSO_4$ and stripped to an oil which solidified on standing. The resulting 1-[3-(4-chlorophenyl)propyl]piperazine (m.p. 54°-62° C.) was used without further purification (b) A mixture of 7.2 g of 1-[3-(4-chlorophenyl)-propyl]piperazine, 2.4 g of 1-bromo-3-chloropropane, 3.5 g of triethylamine and 30 ml of reagent ethanol was refluxed for 6 hours. The solvent was then evaporated under vacuum, and the residue was mixed with 40 ml of water and extracted with ether (3×150 ml). The extract was then evaporated to a yellow oil which was chromatographed on a silica column, the eluant being $CH_2Cl_2/CH_3OH$/ammonium hydroxide (45:5:1). This resulted in 4.6 g (59% of theory) of 1,3-bis[4-(3-{4-chlorophenyl}propyl)-1-piperazinyl]propane as a colorless oil. Part of this oil (3.0 g) was dissolved in 100 ml of ether, and hydrogen chloride-saturated ether was added to this solution until the resulting mixture tested acidic to litmus. The resulting precipitate was dissolved in 25 ml of water, and acetone was added until precipitation appeared complete. This resulted in 2.7 g (41% of theory) of 1,3-bis[4-(3-{4-chlorophenyl}propyl)-1-piperazinyl]propane tetrahydrochloride monohydrate as a white crystalline solid (m.p. 245°-246° C., with decomp.).

EXAMPLE 25

1,3-Bis[4-(4-chloro-3-trifluoromethylbenzyl)-1-piperazinyl]propane tetrahydrochloride A mixture of 11.5 g of 3-chloro-4-trifluoromethylbenzyl chloride, 5.3 g of 1,3-bis(1-piperazinyl)propane, 50 g of reagent ethanol and 7.0 g of triethylamine was refluxed for 16 hours. The reaction mixture was evaporated under reduced pressure, and the residue was mixed with 150 ml of water. The resulting mixture was extracted with ether (5×100 ml). The combined extracts were washed with 1M sodium carbonate solution (3×100 ml). The resulting ether solution was dried over magnesium sulfate, filtered and evaporated to a yellow oil (6.8 g). This oil was dissolved in 100 ml of hexane and filtered. The filtrate was extracted three times with 20 ml of aqueous 2% acetic acid each. The product was found by TLC to be localized in the second and third extracts. These were combined, made strongly basic with 2N NaOH and extracted with 100 ml ether/hexane (1:1). The extract was dried over anhydrous potassium carbonate and then evaporated. The residual oil (2.6 g) in 10 ml of methanol, upon treatment with 30 ml of hydrogen chloride saturated ether, yielded a white precipitate. An additional 50 ml of ether was added and the precipitate was filtered off and recrystallized from methanol to yield colorless crystalline 1,3-bis[4-(4-chloro-3-trifluoromethylbenzyl)-1-piperazinyl]propane tetrahydrochloride (m.p. 265°-268° C., with decomp. >250° C.).

EXAMPLE 26

1,3-Bis[4-(4-hydroxybenzyl)-1-piperazinyl]propane

A mixture of 4.5 g of 1,3-bis[4-(4-methoxybenzyl)-1-piperazinyl]propane from Example 19 and 125 ml of 49% hydrobromic acid was refluxed for 2 hours and was then cooled and diluted with 125 ml of water. After filtration the aqueous solution was neutralized with 2N sodium hydroxide to adjust the pH to 8. The resulting mixture was extracted three times each with 150 ml of ethanol. The alcohol was then removed by rotary evaporation and the residue was chromatographed on silica with the eluant being methylene chloride containing 1% ammonium hydroxide and 10% methanol to obtain 1.3 g (31% of theory) of 1,3-bis[4-(4-hydroxybenzyl)-1-piperazinyl]propane as a white crystalline product, melting at 197°-201° C.

EXAMPLE 27

1,3-Bis[4-(4-bromobenzyl)-1-piperazinyl]propane tetrahydrochloride

A mixture of 3.8 g of 1-(4-bromobenzyl)piperazine, 7 g of ethanol, 1.2 g of 1-bromo-3-chloropropane and 1.6 g of triethylamine was refluxed for 18 hours. The solvent was then removed by rotary evaporation and the residue was mixed with 50 ml of water and sufficient 2N sodium hydroxide to bring the pH above 10. The resulting mixture was extracted twice with ether (75+25 ml) and the combined extract was then washed twice with 25 ml of water, dried over MgSO4 and filtered. To this solution was then added HCl-saturated ether until the mixture remained acidic and the resulting precipitate was filtered off and was mixed with 100 ml of ethanol. The mixture was brought to reflux and water was added dropwise to the refluxing mixture until a solution was formed. Cooling resulted in the crystallization of the product and filtration yielded 4.2 g (81% of theory) of 1,3-bis[4-(4-bromobenzyl)-1-piperazinyl]propane tetrahydrochloride as a white crystalline product melting at 237°-243° C.

EXAMPLE 28

1,3-Bis[4-(4-chlorobenzyl)-1-homopiperazinyl]propane tetrahydrochloride

A mixture of 4.5 g of 1-(4-chlorobenzyl)homopiperazine, 1.6 g of 1-bromo-3-chloropropane and 20 g of ethanol was refluxed for 18 hours. The solvent was removed under vacuum and the mixture was extracted three times with ether (75 ml each) and the extract was evaporated to an oil. This oil was chromatographed on a silica column with the eluant being methylene chloride containing 0.5% concentrated ammonia hydroxide and 2.5% methanol. The fractions containing the product were combined, evaporated to an oil, dissolved in ether and filtered. The resulting ether solution was mixed with hydrogen chloride-saturated ether until the mixture tested acidic to litmus. The resulting precipitate was dried to obtain 1.4 g (22% of theory) of product which after crystallization from aqueous ethanol resulted in 1,3-bis[4-(4-chlorobenzyl)-1-homopiperazinyl]propane tetrahydrochloride as a white crystalline product, melting at 218°-224° C. (decomp.).

EXAMPLE 29

1,3-Bis[4-(4-{4-chlorophenyl}butyl)-1-piperazinyl]propane tetrahydrochloride (a) A mixture of 26.4 g of 4-(4-chlorophenyl)butyl chloride, 86.1 g of anhydrous piperazine and 250 ml of reagent ethanol was refluxed overnight. Solvent was evaporated from the product and the residue was chromatographed twice on silica with the eluant being CH2Cl2/CH3OH/ammonium hydroxide (45:5:1). The first chromatography removed the bulk of the excess piperazine, the second provided 15.2 g of 1-[4-(4-chlorophenyl)butyl]piperazine as a colorless oil which solidified on standing (m.p. 139°-145° C.).

(b) A mixture of 1.5 g of 1-[4-(4-chlorophenyl)butyl]piperazine, 0.5 g of 1-bromo-3-chloropropane, 0.7 g of triethylamine and 10 g of reagent ethanol was refluxed overnight. After addition of 3.5 ml of 2N NaOH, solvent was removed under vacuum. The residue was extracted with methylene chloride and the extract was chromatographed on silica with the eluant being CH2C2/CH3OH/ammonium hydroxide (90:10:1). The product fractions were concentrated to an oil and dissolved in ether. HCl-saturated ether was added precipitating 0.7 g (31%) of 1,3-bis[4-(4-{4-chlorophenyl}butyl)-1-piperazinyl]propane tetrahydrochloride as a light tan solid. Recrystallization from ethanol/water gave a white crystalline solid (m.p. 213°-217° C. decomp.).

EXAMPLE 30

1,3-Bis[4-(4-acetoxybenzyl)-1-piperazinyl]propane

A mixture of 2.0 g of 1,3-bis[4-(4-hydroxybenzyl)-1-piperazinyl]propane (Example 26), 1.0 g of pyridine and 50 g of acetic anhydride was stirred overnight at room temperature. The product mixture was concentrated under vacuum to an amber oil which was mixed with 100 ml of pH 8 phosphate buffer and extracted with ether (3×100 ml). The extract was dried over MgSO4 and stripped to a white solid. Recrystallization from heptane yielded 1.9 g (78%) of 1,3-bis[4-(4-acetoxybenzyl)-1-piperazinyl]propane as a white crystalline solid m.p. 102°-105° C.

EXAMPLE 31

1,3-Bis[4-(4-butoxybenzyl)-1-piperazinyl]propane tetrahydrochloride

A mixture of 1.0 g of 1,3-bis[4-(4-hydroxybenzyl)-1-piperazinyl]propane (from example 26), 10 ml of 2N NaOH, 0.2 g of tetrabutylammonium hydroxide (40% in water) and 5.0 g of 1-bromobutane was heated on a steam bath for 3 hours. The mixture was then extracted with ether (3×75 ml), dried over MgSO₄ and evaporated to a colorless oil which solidified on standing. This product was dissolved in 100 ml of ether and HCl-saturated ether was added until precipitation was complete. Filtration resulted in 1.4 g (91% of theory) of 1,3-bis[4-(4-butoxy-benzyl)-1-piperazinyl]propane tetrahydrochloride as a white solid. Recrystallization from reagent ethanol/water resulted in a white crystalline product (m.p. 207°-218° C.).

EXAMPLE 32

1,3-Bis[4-(4-chlorobenzyl-2,3,5,6-tetramethyl-1-piperazinyl]propane tetrahydrochloride A mixture of 1-(4-chlorobenzyl)2,3,5,6-tetramethyl piperazine, 1 g of 1-bromo-3-chloropropane, and 1 g of triethylamine is heated under reflux in 20 ml of ethanol for 24 hours and the reaction mixture is evaporated under reduced pressure to an oil. The residue is dissolved in water and extracted with ether. The ether extract is washed with water and dried over magnesium sulfate. The product is precipitated from the ether solution by precipitation with excess ethereal hydrogen chloride and crystallization from ethanol to provide 1,3-bis[4-(4-chlorobenzyl)-2,3,5,6-tetramethyl-1-piperazinyl]propane tetrahydrochloride as a white crystalline solid.

EXAMPLE 33

1-[4-(4-chlorobenzyl)-1-piperazinyl]-3-[4-(2-carboxy-2-phenylethyl)-1-piperazinyl]propane tetrahydrochloride A suspension of 340 mg of 1-[4-(4-chlorobenzyl)-1-piperazinyl]-3-[4-(2-ethoxycarbonyl-2-phenylethyl)-1-piperazinyl]propane tetrahydrochloride in 10 ml of ethanol was treated with 1 ml of aqueous 5M sodium hydroxide and heated under reflux for 1 hour. The reaction mixture was evaporated to dryness under reduced pressure. The residue was mixed with 1N hydrochloric acid (3 ml) and the resulting mixture extracted with ether (2×10 ml). The extract was discarded and the pH of aqueous phase adjusted to 5.5 with 1N hydrochloric acid. Aqueous saturated sodium chloride solution (10 ml) was added and the mixture extracted with butanol (2×10 ml). The butanol extract was filtered and treated with excess ethereal hydrogen chloride. The white precipitate was collected and recrystallized from aqueous ethanol to yield 1-[4-(4-chlorobenzyl)-1-piperazinyl]-3-[4-(2-carboxy-2-phenylethyl)-1-piperazinyl]propane tetrahydrochloride (140 mg, 40% yield) as a white crystalline solid (m.p. 230°-245° C. decomp.).

EXAMPLE 34

1,3-Bis[4-(3-{4-chlorophenyl}propyl]-1-homopiperazinyl]propane tetrahydrochloride A mixture of 3.8 g of 1-[3-(4-chlorophenyl)propyl]-homopiperazine, 1.2 g of 1-bromo-3-chloropropane, 1.8 g of triethylamine is heated under reflux in 10 ml of ethanol for 18 hours and the reaction mixture evaporated to dryness under reduced pressure. The residue is mixed with water and extracted with ether. The ether extract is evaporated and the residue chromatographed on silica gel [CH₂Cl₂/CH₃OH/NH₄OH (35:5:1)]. The resulting oil is dissolved in ether and the product precipitated with excess ethereal hydrogen chloride. Crystallization from ethanol provides 1,3-bis[4-(3-{4-chlorophenyl}propyl)-1-homopiperazinyl]propane tetrahydrochloride as a crystalline solid.

EXAMPLE 35

1,3-Bis[4-(4-chlorobenzyl)-1-homopiperazinyl]-1,3-dioxopropane dihydrochloride 0.7 g of malonyl dichloride is added at once to a solution of 2.2 g of 1-(4-chlorobenzyl)homopiperazine and 1 g of triethylamine in 10 ml of methylene chloride at room temperature and the reaction mixture heated under reflux for one hour and then evaporated under reduced pressure. The residue is triturated with water and the crude product extracted with methylene chloride and purified by chromatography on silica [CH₂CL₂/CH₃OH/NH₂OH (200:5:1)]. The appropriate fractions are evaporated, dissolved in ether and treated with excess ethereal hydrogen chloride to obtain 1,3-bis[4-(4-chlorobenzyl)-1-homopiperazinyl]-1,3-dioxopropane dihydrochloride as a crystalline solid.

EXAMPLE 36

The in vitro inhibition of histamine release from human leukocytes (basophils), from rat peritoneal mast cells, and from guinea pig basophils by the compounds of formula I can be demonstrated according to the following biochemical test procedures:

A. Procedure for Determining Inhibition of Histamine Release from Human Leukocytes (Basophils)

1. Separation of Leukocytes: A modification of the method of L. Lichtenstein and A. Osler, *J. Exp. Med.* 120, 507 (1964) is used. Heparinized human blood (80–100 ml) is mixed with 20 ml of saline (0.2%) containing 0.6 gm of dextrose and 1.2 gm dextran in propylene centrifuge tubes. The mixture is kept at ambient temperature for 60–90 minutes to allow the separation of erythrocytes from the platelet-leukocyte-rich supernate. The supernate is removed and centrifuged for 8 minutes at 110×g in cold. The leukocyte pellet is washed twice with Tris buffer and finally suspended in 150–180 ml Tris-ACM buffer at 1–2×10⁶ cells/ml.

2. Reaction Mixture: The reaction is carried out in 12×75 mm plastic tubes at a total volume of 1.23 ml. The reaction medium includes 0.05 ml rabbit anti-human IgE (the antigen), 0.2 ml of the test compound in water at concentrations ranging from 10–100 μM, and 0.1 ml of the leukocyte suspension. The reaction mixture is incubated in a 37° C. shaking water bath for 60 minutes. Upon completion of the reaction, the tubes are centrifuged and the supernatants collected. The protein is removed from the supernatants by precipitation with 0.2 ml of 8% perchloric acid.

3. Histamine Assay: Histamine release is measured by the automated fluorometric method of W. Siraganian and W. Hook in Chapter 102 of the *Manual of Clinical Immunology*, 2nd Edition, edited by R. Rose and H. Friedman, published by the American Society for Microbiology, Washington, D.C. 1980. Percent inhibition is calculated as follows:

$$\frac{(Control - blank) - (Test\ sample - blank)}{(Control - blank)} \times 100$$

The concentration which causes a 50 percent inhibition (IC₅₀) of histamine release is interpolated from a plot of percent inhibition versus logarithm of drug concentration.

B. Procedure for Determining Inhibition of Histamine Release from Rat Peritoneal Mast Cells 1. Harvest of Peritoneal Mast Cells: After the rats are sacrificed with ether, 20 ml of Minimum Essential Medium (MEM) containing 20 units/ml heparin is injected into the peritoneum. The abdomen is massaged for one minute and the lavage fluid collected. The peritoneal cells are centrifuged at 1800 rpm for 8 minutes in cold. After two washes with Tris A buffer, the cells are resuspended in Tris ACM buffer at $2-4 \times 10^6$ cells/ml.

2. Reaction Mixture: The reaction is carried out in $12 \times 75$ mm plastic tubes at a total volume of 1.25 ml. The reaction mixture includes 0.5 ml (10–1000 μg) sheep anti-rat IgE or ovalbumin, 0.2 ml of the test compound in water at concentrations ranging from 10–1000 μM, 0.5 ml phosphatidylserine solution (20–60 μg to each tube), and 0.5 ml of cell suspension.

The reaction mixture is incubated in a 37° C. shaking water bath for 60 minutes. Upon completion of the reaction, the tubes are centrifuged and the supernatants collected. The protein is removed from the supernatants by precipitation with 0.2 ml of 8% perchloric acid.

3. Histamine Assay: Histamine release is measured by the automated fluorometric method of Siraganian, supra.

The concentration which causes a 50% inhibition ($IC_{50}$) of histamine release is computed as in Part A.

C. Procedure for Determining Inhibition of Histamine Release from Guinea Pig Basophils 1. In Vivo Sensitization: Male Hartley guinea pigs (200–300 gms) are immunized on day 0 with two 0.05 ml intradermal injections of 200 μg ovalbumin. Sensitized basophils are available between days 13–25 post-sensitization. This mode of sensitization favors IgE response.

2. Separation of Leukocytes: The method of Lett-Brown et al., *Int. Arch. Allergy, Appl. Immun.* 64, 241 (1981) is used. Animals are anesthetized with ether and are bled via cardiac puncture with plastic syringes containing sufficient EDTA to provide a final concentration of 10 mM.

One part of 3% gelatin in saline at 37° C. is mixed with two parts of blood in a $16 \times 150$ mm tube. The cells are allowed to sediment at a 30° angle for 45 minutes in a 37° C. water bath. The leukocyte-rich plasma is collected and centrifuged at $150 \times g$ for 30 minutes at room temperature. The pelleted cells are washed in Hepes-buffered saline (HG) containing 4 mM EDTA and resuspended in Hepes-buffered saline containing $Mg^{++}$ and $Ca^{++}$ (HGCM) at $4-5 \times 10^6$ cells/ml.

3. Reaction Mixture: The reaction is carried out in $12 \times 75$ mm plastic tubes and a total volume of 1.2 ml which includes 0.5 ml of antigen, 0.2 ml of drug solution at concentrations ranging from 10–1000 μM and 0.5 ml of prewashed cell suspension. The reaction mixture is incubated in a 37° C. shaking water bath for 60 minutes. Upon completion of the reaction, the tubes are centrifuged and the supernatants collected. The protein is removed from the supernatants by precipitation with 0.2 ml of 8% perchloric acid.

4. Histamine Assay: Histamine release is measured by the automated fluorometric method of Siraganian, supra. The concentration which causes a 50 percent inhibition of Histamine release is computed as in Part A.

The results of the testing of compounds of formula I for the inhibition of histamine release from human leukocytes (basophils) according to Procedure A, from rat peritoneal mast cells according to Procedure B, and from guinea pig basophils according to Procedure C, are shown in TABLE 1 below:

TABLE 1

| Test Compound (Example No.) | In Vitro Inhibition of Histamine Release $IC_{50}$ (μM) | | |
|---|---|---|---|
| | Procedure A[a] | Procedure B[b] | Procedure C[c] |
| 1 | 11 | 2 | 35 |
| 2 | 12 | 80 | 23 |
| 3 | 24 | NS | NS |
| 4 | 53 | NS | NS |
| 5 | 45 | NS | 760 |
| 6 | 12 | NS | NS |
| 7 | 4 | NS | NS |
| 8 | >1000[d] | >100[d] | NS |
| 9 | 10 | NS | NS |
| 10 | 3 | NS | NS |
| 11 | 20 | NS | NS |
| 12 | 800 | NS | NS |
| 13 | ~1000 | NS | NS |
| 14 | 28 | NS | NS |
| 15 | 17 | 10 | 49 |
| 16 | 3 | >100[d] | 12 |
| 17 | 80 | NS | NS |
| 19 | 100 | NS | NS |
| 20 | 3 | NS | NS |
| 21 | 14 | NS | NS |
| 22 | 20 | NS | NS |
| 23 | 14 | NS | NS |
| 24 | 2 | 2 | 8.9 |
| 25 | 6 | NS | NS |
| 26 | >1000[d] | NS | NS |
| 27 | 3 | NS | NS |
| 28 | 6 | 9 | 2.3 |
| 29 | 2 | NS | NS |
| 30 | >1000[d] | NS | NS |
| 31 | 4 | NS | NS |
| 32 | 1000 | NS | NS |

NS = Not submitted for testing
[a] From human basophils.
[b] From rat peritoneal mast cells.
[c] From guinea pig basophils.
[d] No response detected at highest dose indicated.

EXAMPLE 37

Topical solution (ophthalmic or nasal)

The solution composition is compounded from the following ingredients:

| | |
|---|---|
| 1,3-Bis[4-(3-{4-chlorophenyl}propyl)-1-piperazinyl]propane tetrahydrochloride monohydrate | 0.100 g |
| Disodium hydrogen phosphate.7 $H_2O$ | 1.073 g |
| Dihydrogen sodium phosphate.$H_2O$ | 0.386 g |
| Sodium chloride | 0.387 g |
| Distilled water q.s.ad | 100.00 ml |

The ingredients are dissolved in the conventional manner to form an aqueous solution. The solution is appropriately filtered, with the opthalmic solution requiring sterile filtration. Each ml of the solution contains 1.0 mg of the active ingredient.

EXAMPLE 38

Ointment

The ointment composition utilizes the following base compounded in a conventional manner

| | |
|---|---|
| White petrolatum | 75 g |
| Mineral oil | 25 g |
| White wax | 2 g |

The active ingredient, for example 1,3-Bis[4-(3-{4-chlorophenyl}propyl)-1-piperazinyl]propane tetrahydrochloride monohydrate, is uniformly incorporated into the base at the required concentration, for example, 1 g of the active ingredient can be incorporated into 100 g of base.

EXAMPLE 39

Inhalation aerosol

The aerosol composition is compounded from the following ingredients:

| | |
|---|---|
| 1,3-Bis[4-(3-{4-chlorophenyl}propyl)-1-piperazinyl]propane tetrahydrochloride monohydrate | 1.00 parts |
| Soybean lecithin | 0.20 parts |
| Propellant gas mixture (Freon 11, 12 and 14) q.s.ad | 100.00 parts |

The ingredients are compounded in conventional manner, and the composition is filled into aerosol containers with a metering valve which releases 0.5 to 2.0 mg of active ingredient per actuation of the valve.

Any one of the other compounds embraced by formula I or a non-toxic, pharmacologically acceptable acid addition salt thereof may be substituted for the particular active ingredient in Examples 37 through 39. Likewise, the amount of active ingredient in these illustrative examples may be varied to achieve the desired dosage unit range, and the amounts and nature of the inert pharmaceutical carrier ingredient may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit or the scope of the appended claims.

We claim:

1. The compound which is 1,3-bis[4-(4-chlorobenzyl)-1-piperazinyl]-2-hydroxypropane.

2. The compound which is 1,3-bis[4-(4-fluorobenzyl)-1-piperazinyl]propane.

3. The compound which is 1,3-bis[4-(4-chlorobenzyl)-1-piperazinyl]-1-oxo-propane.

4. The compound which is 1,3-bis(4-(4-chlorobenzyl)-1-piperazinyl]-1-methylpropane.

5. The compound which is 1-[4-(4-chlorobenzyl)-1-piperazinyl]-3-[4-(2-ethoxycarbonyl-2-phenyhlethyl)-1-ethoxycarbonylpiperazinyl-1-methyl]propane.

6. The compound which is 1-[4-(4-chlorobenzyl)-1-piperazinyl]-3-(4-phenacyl-1-piperazinyl)propane.

7. The compound which is 1-[4-(4-chlorobenzyl)-1-piperazinyl]-3-[4-(2-hydroxy-2-phenylethyl)-1-piperazinyl]propane.

8. The compound which is 1,3-bis(4-phenacyl-1-piperazinyl)propane.

9. The compound which is 1,3-bis(4-phenethyl-1-piperazinyl)propane.

10. The compound which is 1,3-bis[4-(4-chlorobenzyl)-1-piperazinyl[-1,3-dioxopropane.

11. The compound which is 1,3-bis[4-(4-chlorophenethyl)-1-piperazinyl]propane.

12. The compound which is 1,3-bis[4-(4-(1-phenethyl)-1-piperazinyl]propane.

13. The compound which is 1,3-bis[4-(3,4-dichlorobenzyl)-1-piperazinyl]propane.

14. The compound which is 1,3-bis(4-(3-{4-chlorophenyl}propyl)-1-piperazinyl]propane.

15. The compound which is 1,3-bis[4-(4-chloro-3-trifluoromethylbenzyl)-1-piperazinyl]propane.

16. The compound which is 1,3-bis[4-(4-bromobenzyl)-1-piperazinyl]propane.

17. The compound which is 1,3-bis[4-(4-chlorobenzyl)-1-homopiperazinyl]propane.

18. The compound which is 1,3-bis[4-(4-{4-chlorophenyl}butyl-1-piperazinyl]propane.

19. A topical antiallergic or anti-inflammatory pharmaceutical composition comprising an inert pharmaceutical carrier and an effect antiallergic or anti-inflammatory amount of a compound of claim 14.

20. The method of suppressing allergic reactions or inflammation in a warm-blooded animal in need thereof, which comprises topically administering to said animal an effective antiallergic or anti-inflammatory amount of a compound of claim 14.

* * * * *